United States Patent [19]

Distler et al.

[11] 4,107,500
[45] Aug. 15, 1978

[54] TIME SWITCH DEVICE FOR X-RAY DIAGNOSTIC EQUIPMENT

[75] Inventors: Georg Distler, Adlitz; Horst Göetzl, Erlangen, both of Germany

[73] Assignee: Siemens Aktiengesellschaft, Berlin & Munich, Germany

[21] Appl. No.: 720,459

[22] Filed: Sep. 3, 1976

[30] Foreign Application Priority Data

Oct. 6, 1975 [DE] Fed. Rep. of Germany ....... 2544697

[51] Int. Cl.² .................... H01H 9/00; G01P 13/00; G09F 9/00
[52] U.S. Cl. .................................. 200/308; 116/115; 116/133; 200/336
[58] Field of Search ............... 200/308, 316, 155 R, 200/156, 336, 155 A, 5 B, 179, 180; 116/115, 115.5, 124 L, 129 F, 129 T, 133

[56] References Cited

U.S. PATENT DOCUMENTS

| 3,013,339 | 12/1961 | Brewer et al. | 116/115 X |
|---|---|---|---|
| 3,198,923 | 8/1965 | Tripp | 200/308 |
| 3,720,800 | 3/1973 | Arnold | 200/308 |
| 3,890,716 | 6/1975 | Hatch | 116/115 X |
| 4,013,036 | 3/1977 | Grassme' | 116/133 X |

Primary Examiner—William Price
Assistant Examiner—Steven M. Pollard
Attorney, Agent, or Firm—Hill, Gross, Simpson, Van Santen, Steadman, Chiara & Simpson

[57] ABSTRACT

A time switch device for X-ray diagnostic apparatus, in particular for the preparation of a tooth or dental exposure characterized by the device including a housing, a knob mounted on the housing for rotation to set the exposure period, a time scale of exposure periods concentrically arranged to the knob, a symbol carrier concentrically arranged to the knob. The symbol carrier has a symbol of each object being X-rayed arranged thereon one relative to the other at such a spacing relative to each other so that upon setting one of the symbols to the exposure period that is associated therewith, the other symbols will be located opposite their respective associated exposure periods on the time scale. The knob is movable in an axial direction and the symbol carrier and knob have coacting coupling means which will become engaged when the knob assumes a predetermined axial position to couple the symbol carrier for rotational movement with the knob.

8 Claims, 2 Drawing Figures

TIME SWITCH DEVICE FOR X-RAY DIAGNOSTIC EQUIPMENT

BACKGROUND OF THE INVENTION

1. Field of the Invention

The present invention relates to a time switch device for a X-ray diagnostic apparatus, in particular for the preparation of a dental exposure, having a rotary knob for setting the exposure time, a time scale concentrically arranged relative to the knob, a symbol carrier concentrically arranged to the knob and adjustable in relative positions of rotation relative to the time scale and the knob. The symbol carrier has symbols of the objects being X-rayed arranged thereon one relative to the other at such a spacing relative to each other so that upon setting one of the symbols to the exposure period associated therewith, the other symbols will be located opposite their respective associated exposure periods on the time scale.

2. Prior Art

A time switch device having a rotatable knob, a scale carrier concentrically arranged relative to the knob and a symbol carrier concentrically arranged to the knob and movable relative to the time scale and the knob is disclosed in a co-pending U.S. patent application Ser. No. 631,612, filed Mar. 13, 1975, which issued as U.S. Pat. No. 4,013,036 and corresponds to German patent application No. P 24 61 263.3. The symbol carrier has symbols of the object to be X-rayed arranged thereon one relative to the other with a selected spacing therebetween so that upon setting one of the symbols to the exposure period associated therewith, the other symbols will be located opposite their respective associated exposure periods on the time scale. With this device, the exposure data can be adjusted in a very simplified manner. It is necessary to first set the symbol carrier by rotating it relative to the knob and time scale so that one of the symbols is at the desired exposure time or period for the object represented by that symbol. With such adjustment of the symbol carrier, each of the other symbols will be located at the desired exposure period or time for their respective objects. During exposure, a mark on the knob is rotated to be aligned with the desired symbol of the object to be X-rayed and then the timer will provide the correct amount of exposure. This time switch device permits the selecting of the exposure time on the basis of the object symbol.

SUMMARY OF THE INVENTION

The present invention has the object of creating an especially simple, easy and clearly operable embodiment of a time switch device which is an improvement over the known time switch devices for X-ray diagnostic apparatus particularly for the preparation of dental exposures. To accomplish this task, a time switch device, which has a housing, a knob mounted on the housing for rotation to set exposure periods, a time scale of exposure periods on a scale carrier concentrically arranged to the knob, a symbol carrier concentrically arranged to the knob and being mounted for rotation relative to the time scale and the knob, said symbol carrier having symbols of the objects being X-rayed being arranged thereon one relative to the other at a spacing relative to each other so that upon setting one of said symbols to the exposure period associated therewith, the other symbols will be located opposite their respective associated exposure periods on the time scale, has the improvements comprising the knob being movable in an axial direction and said symbol carrier and said knob having coupling means being engaged with each other as the knob assumes a predetermined axial position to couple the symbol carrier for rotational movement with the knob. The improvement in the time switch device enables the knob, which sets the desired exposure time, to be in addition coupled to the symbol carrier to adjust the position of the symbol carrier relative to the time scale. This improvement of the time switch device thus enables making adjustments in the time switch device utilizing a minimum number of elements.

In the preferred embodiment, the symbol carrier is a disk-shaped ring and the device includes a second disk-shaped ring of transparent material concentrically mounted relative to the knob and constantly coupled thereto. The second disk-shaped ring covers or overlies the symbol carrier and is provided with at least one mark which is utilized as an indicia for the knob to indicate the desired exposure time. Preferably, the second disk has a plurality of spaced marks which are circumferentially spaced on the second disk-shaped ring with the spacing between the marks being selected so that each of the plurality of marks corresponds to a given thickness of the object being X-rayed. Since the second disk-shaped ring overlies or covers the symbol carrier, it protects the symbol carrier from being unintentionally displaced due to an accidental touching of the symbol carrier by the operator of the timing switch device.

DESCRIPTION OF THE PREFERRED EMBODIMENT

Figure 1:
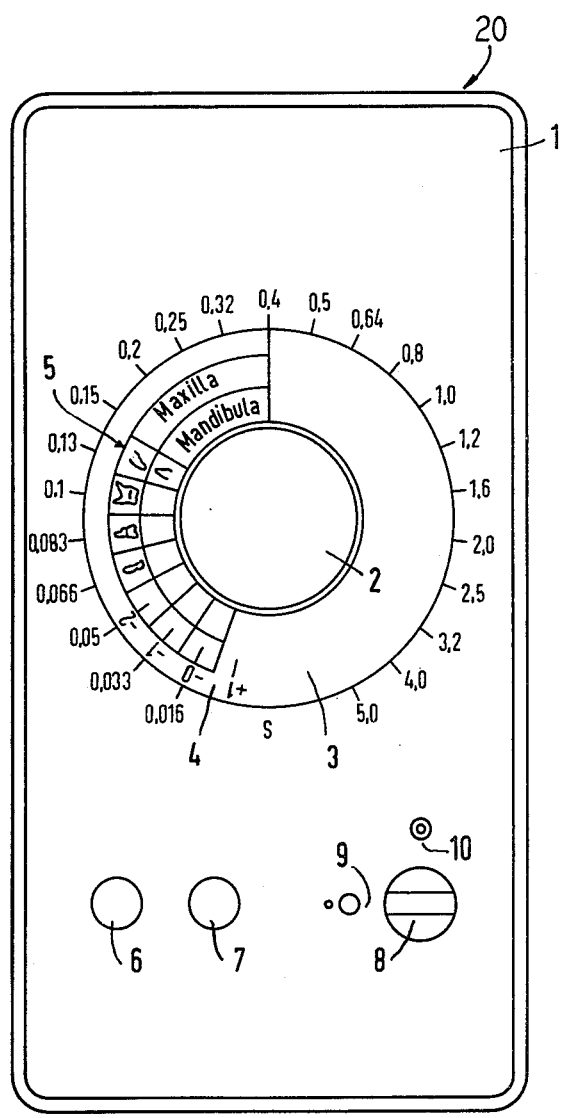
FIG. 1 is a front view of a time switch device in accordance with the present invention.

The principles of the present invention are particularly useful when incorporated in a time switch device generally indicated at 20 in the figures.

The time switch device 20 has a housing with a front plate 1 which supports an operating knob 2 that is used to select the desired exposure times. The knob 2 is continuously coupled to a disk-shaped ring 3 of transparent material which ring has four circumferentially spaced marks identified as +1, 0, −1 and −2. The front plate 1 is a time scale carrier which has a time scale of exposure periods which surround the disk 3 and is concentric with the axis of the knob 2.

Beneath the disk-shaped ring or disk 3 is a symbol carrier 4 which is also constructed as a disk-shaped ring. The symbol carrier 4 has tooth symbols for the upper jaw (maxilla) and lower jaw (mandibula) which are arranged in the field generally indicated at 5. The symbol carrier 4 is normally not rotated when the knob 2 is turned to set a given exposure time. To rotate the symbol carrier 5, the knob 2 is depressed axially in the direction of the front plate 1 to couple the symbol carrier 4 to the knob 2 for movement therewith.

In addition to the knob 2, the time scale and the symbol carrier 4 with the cover ring 3, the front plate 1 of the housing of the time switch device 20 has two monitoring lamps 6 and 7 and an operating switch 8. The operating switch 8, which is associated with a switching mechanism 17 (FIG. 2), can be moved alternately between two positions 9 and 10 and the operating switch will permit a switch on and off of the time switch device. The switch 8 may be constructed as a key switch with a key which can be removed when the switch 8 is in an off position to lock the time switch device 20 in an inoperative or off condition.

Figure 2:
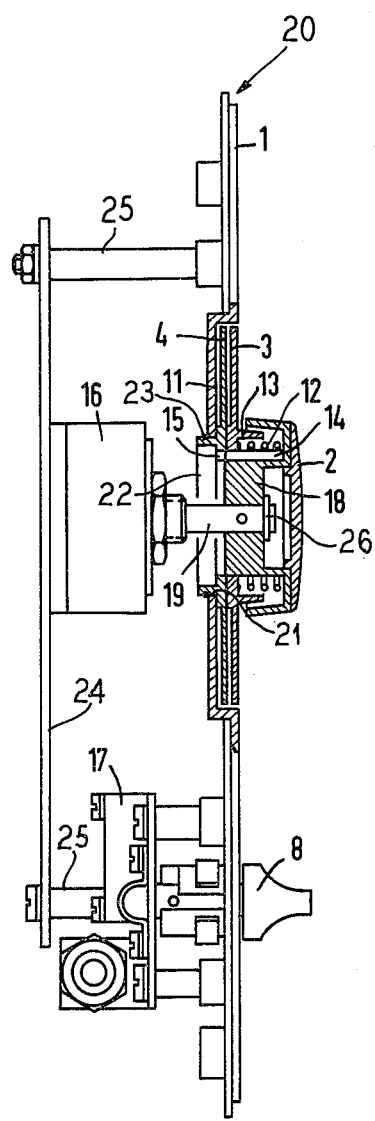
FIG. 2 is a side view with portions removed and portions broken away for purposes of illustration of the time switch device of FIG. 1.

As best illustrated in FIG. 2, the front plate 1 has a depression 11 with a concentrically disposed aperture 21. The symbol carrier 4 has a concentric cylindrical projection or hub 22 which is rotatably received in the aperture 21 and held therein by a ring member 23 so that the disk-shaped portion is received in the depression 11 and covered by the disk-shaped ring 3 which is also received in the depression 11.

The knob 2 has a body portion 18 and is mounted for axial movement on a shaft 19 of electronic component 16 of the time switch. As illustrated, the component 16 is mounted on a plate 24 that is secured in spaced relationship to the front plate 1 by posts or pins 25. Thus, a rotation of the knob 2 will rotate the shaft 19 to set the desired exposure time in the electronic component 16.

To hold the knob 2 in its outermost axial position against a stop washer or ring 26 of the shaft 19, biasing means such as the spring 12 is entrapped between the knob 2 and the transparent disk-shaped member 3 which has a cylindrical projection 13 surrounding a portion of the spring 12. To form the coupling means, the body 18 of the knob has rib-shaped projections 14 (only one is illustrated). These rib-shaped projections 14 are received in matching grooves of the disk 3 so that the knob 2 is continuously coupled with the ring 3. However, the projections and grooves of the knob 2 and the ring 3 allow axial movement therebetween. The symbol carrier 4 is also provided with grooves 15 (only one is illustrated) which can receive the projections 14 of the knob 2. In the outer withdrawn position (illustrated in FIG. 2), the projections 14 are axially withdrawn from the grooves 15 of the symbol carrier 4. Thus, rotation of the knob will not cause any rotation of the symbol carrier 4, although the ring 3 will rotate with the rotation or turning of the knob 2.

If the knob 2 is depressed axially in the direction toward the plate 1, the projections or ribs 14 will come into engagement with the corresponding grooves 15 and form coacting coupling means which, when engaged, couple the symbol carrier 4 to rotate with the knob 2.

When placing the timing device in operation, the user of the timing switch device 20 will adjust the position of the symbol carrier 4 relative to the time scale on the front plate 1. This is accomplished by depressing the knob 2 to couple the knob 2 to the symbol carrier 4. It is noted that the knob 2 may need to be rotated slightly to align the projections 14 with the grooves or notches 15 of the symbol carrier 4. With the knob 2 depressed and the symbol carrier 4 coupled to the knob, the symbol carrier 4 may be rotated until one of the symbols of the object to be X-rayed, such as teeth, in the field 5 is located opposite the correct exposure time which is assigned to it. With the aligning of one of the tooth symbols with its correct exposure time, each of the other tooth symbols will be positioned opposite the exposure times assigned to them. After positioning the symbol carrier 4 in the desired position, releasing of the knob 2 will disengage the coupling between the knob 2 and the symbol carrier. Subsequently, if the exposure is to be made, the user only needs to rotate the knob 2, without depressing it, until the desired mark on the transparent ring 3, which is usually the zero mark, is located opposite the symbol for the type of tooth being X-rayed. The timing switch device 20 will then ensure a correct duration or exposure period when the X-ray device is triggered. If the patient has a thick jaw, the +1 mark is placed on the desired symbol for the tooth being X-rayed instead of the 0 mark. For thin or weak jaws, the −1 mark is utilized and for very thin or very weak jaws, a −2 mark is used. The spacing of marks +1, 0 −2 and −2 are such to compensate the length of the exposure time for variations due to jaws thicker or heavier than normal and jaws or bone structure which is thinner than normal.

The operation of the time switch device 20 is very simple. By means of a single knob 2, the selection of the desired exposure times and the setting of the carrier symbol 4 is possible. A requirement for the adjustment of the symbol carrier 4 only occurs rarely and usually occurs when the main voltage deviates considerably from the nominal value or in order to compensate for any aging effects in the X-rayed tube. Thus, once the symbol carrier 4 is adjusted to match the desired exposure time to a particular symbol for an object being X-rayed, a large series of X-rays can be taken of different teeth without requiring re-adjustment of the position of the symbol carrier.

Although various minor modifications may be suggested by those versed in the art, it should be understood that we wish to employ within the scope of the patent warranted hereon, all such modifications as reasonably and properly come within the scope of our contribution to the art.

We claim:

1. In a time switch device for X-ray diagnostic apparatus, particularly for preparation of dental exposures, said device including a housing, a knob mounted on the housing for rotation to set the exposure period, a time scale of exposure periods on a scale carrier concentrically arranged to the knob, a symbol carrier concentrically arranged to the knob and being mounted for rotation relative to the time scale, said symbol carrier having symbols of the objects being X-rayed arranged thereon one relative to the other at such a spacing relative to each other so that upon setting one of said symbols to the exposure period associated therewith, the other symbols will be located opposite their respective associated exposure periods on the time scale, and an indicia of at least one mark so that rotation of the knob to set the exposure period causes relative movement between the indicia and both the symbol carrier and time scale, the improvements comprising said knob being movable in an axial direction, and said symbol carrier and said knob having coupling means being engaged with each other as the knob assumes a predetermined axial position to couple the symbol carrier for rotational movement with said knob.

2. In a time switch device according to claim 1, wherein the symbol carrier is a disk-shaped ring, wherein the scale carrier is a portion of the housing of the time switch and the time scale of exposure periods concentrically surrounds the symbol carrier, and which device includes a second disk-shaped ring of transparent material concentrically mounted relative to the knob and constantly coupled thereto, said second disk-shaped ring overlying the symbol carrier and being provided with the indicia of at least one mark to be set to the time scale.

3. In a time switch device according to claim 2, wherein said second disk-shaped ring has a plurality of marks circumferentially spaced thereon with the spacing between the marks being selected so that each of said plurality of marks correspond to a given thickness of an object being X-rayed.

4. In a time switch device according to claim 1, wherein said predetermined axial position is an inner axial position with the knob moved axially toward the housing and said coupling means being positioned on said knob and said symbol carrier so that engagement occurs as the knob is moved axially toward the housing.

5. In a time switch device according to claim 4, wherein the symbol carrier is a disk-shaped ring, wherein the scale carrier is a portion of the housing of the time switch and the time scale of exposure periods concentrically surround the symbol carrier, and which device includes a second disk-shaped ring of transparent material concentrically mounted relative to the knob and constantly coupled thereto, said second disk-shaped ring overlying the symbol carrier and being provided with the indicia of at least one mark to be set to the time scale.

6. In a time switch device according to claim 5, wherein said second disk-shaped ring has a plurality of marks circumferentially spaced thereon with the spacing between the marks being selected so that each of said plurality of marks corresponds to a given thickness of an object being X-rayed.

7. In a time switch device according to claim 5, which includes biasing means acting on the knob to move it axially to an outward position with the coupling means disengaged so that the knob is forced against the biasing means to the inner position with the coupling means in engagement.

8. In a time switch device according to claim 7, wherein the knob moves relative to the second disk-shaped ring and said biasing means acts between the disk-shaped ring and said knob.

* * * * *